(12) United States Patent
Shelton, IV et al.

(10) Patent No.: US 10,709,473 B2
(45) Date of Patent: Jul. 14, 2020

(54) TROCAR OBTURATOR WITH DETACHABLE ROTARY TISSUE FASTENER

(71) Applicant: ETHICON LLC, Guaynabo, PR (US)

(72) Inventors: Frederick E. Shelton, IV, Hillsboro, OH (US); Jason L. Harris, Lebanon, OH (US); Nicholas W. Seipelt, Milford, OH (US); David T. Martin, Milford, OH (US); Zhifan F. Huang, Mason, OH (US)

(73) Assignee: Ethicon LLC, Guaynabo, PR (US)

( * ) Notice: Subject to any disclaimer, the term of this patent is extended or adjusted under 35 U.S.C. 154(b) by 76 days.

(21) Appl. No.: 15/637,735

(22) Filed: Jun. 29, 2017

(65) Prior Publication Data
US 2019/0000502 A1    Jan. 3, 2019

(51) Int. Cl.
*A61B 17/34* (2006.01)
*A61B 17/00* (2006.01)
(Continued)

(52) U.S. Cl.
CPC ...... *A61B 17/3417* (2013.01); *A61B 17/0057* (2013.01); *A61B 17/0644* (2013.01);
(Continued)

(58) Field of Classification Search
CPC . A61B 17/068; A61B 17/064; A61B 17/0644; A61B 17/0682;
(Continued)

(56) References Cited

U.S. PATENT DOCUMENTS 5,478,354 A    12/1995    Tovey et al.
5,792,135 A    8/1998    Madhani et al.
(Continued)

FOREIGN PATENT DOCUMENTS

FR    2 719 993 A1    11/1995
WO    WO 2009/135022 A1    11/2009

OTHER PUBLICATIONS

U.S. Appl. No. 15/637,690, filed Jun. 29, 2017.
(Continued)

*Primary Examiner* — Diane D Yabut
*Assistant Examiner* — Majid Jamialahmadi
(74) *Attorney, Agent, or Firm* — Frost Brown Todd LLC

(57) ABSTRACT

A surgical instrument includes a shaft and a tissue fastener. The tissue fastener is releasably attached to the distal end portion of the shaft. The shaft is operable to rotatably drive the tissue fastener about a longitudinal axis of the shaft. The tissue fastener includes a base, first and second arms, and barbs. The first and second arms extend laterally and longitudinally from the base and are configured to be received within a first and second tissue portion, respectively. The first and second arms are configured to draw the first tissue portion against the second tissue portion. The barbs extend from the first and second arms and are configured to anchor the first and second arms within the first and second tissue portions. The shaft is configured to release the tissue fastener thereby securing the first tissue portion against the second tissue portion with the tissue fastener anchored therein.

19 Claims, 11 Drawing Sheets

(51) Int. Cl.
  *A61B 17/064* (2006.01)
  *A61B 17/128* (2006.01)
  *A61B 17/068* (2006.01)
  *A61B 17/10* (2006.01)

(52) U.S. Cl.
  CPC ...... *A61B 17/1285* (2013.01); *A61B 17/3421* (2013.01); *A61B 17/068* (2013.01); *A61B 17/3474* (2013.01); *A61B 2017/00637* (2013.01); *A61B 2017/00663* (2013.01); *A61B 2017/00668* (2013.01); *A61B 2017/0645* (2013.01); *A61B 2017/0649* (2013.01); *A61B 2017/346* (2013.01); *A61B 2017/3454* (2013.01)

(58) Field of Classification Search
  CPC .. A61B 2017/00668; A61B 2017/0649; A61B 2017/081
  See application file for complete search history.

(56) References Cited

U.S. PATENT DOCUMENTS

| | | | |
|---|---|---|---|
| 5,817,084 | A | 10/1998 | Jensen |
| 5,878,193 | A | 3/1999 | Wang et al. |
| 6,231,565 | B1 | 5/2001 | Tovey et al. |
| 6,364,888 | B1 | 4/2002 | Niemeyer et al. |
| 6,783,524 | B2 | 8/2004 | Anderson et al. |
| 7,524,320 | B2 | 4/2009 | Tierney |
| 7,691,098 | B2 | 4/2010 | Wallace et al. |
| 7,806,891 | B2 | 10/2010 | Nowlin et al. |
| 7,981,092 | B2 | 7/2011 | Duke |
| 8,226,553 | B2 | 7/2012 | Shelton, IV et al. |
| 8,251,900 | B2 | 8/2012 | Ortiz et al. |
| 8,479,969 | B2 | 7/2013 | Shelton, IV |
| 8,568,362 | B2 | 10/2013 | Moreno et al. |
| 8,573,461 | B2 | 11/2013 | Shelton, IV et al. |
| 8,573,465 | B2 | 11/2013 | Shelton, IV |
| 8,579,807 | B2 | 11/2013 | Moreno et al. |
| 8,602,288 | B2 | 12/2013 | Shelton, IV et al. |
| 8,616,431 | B2 | 12/2013 | Timm et al. |
| 8,636,686 | B2 | 1/2014 | Minnelli et al. |
| 8,690,831 | B2 | 4/2014 | Duke |
| 8,783,541 | B2 | 7/2014 | Shelton, IV et al. |
| 8,800,838 | B2 | 8/2014 | Shelton, IV |
| 8,820,605 | B2 | 9/2014 | Shelton, IV |
| 8,844,789 | B2 | 9/2014 | Shelton, IV et al. |
| 9,295,463 | B2 | 3/2016 | Viola et al. |
| 9,301,759 | B2 | 4/2016 | Spivey et al. |
| 9,687,226 | B2 | 6/2017 | Hodgkinson et al. |
| 9,700,303 | B2 | 7/2017 | Prior et al. |
| 10,045,842 | B2 | 8/2018 | Alexander et al. |
| 2007/0186933 | A1* | 8/2007 | Domingo et al. ............ A61B 17/12022 128/207.15 |
| 2008/0200950 | A1 | 8/2008 | Wohlert |
| 2008/0208265 | A1* | 8/2008 | Frazier ............... A61B 17/0401 606/326 |
| 2009/0275957 | A1* | 11/2009 | Harris ................ A61B 17/064 606/142 |
| 2012/0071566 | A1* | 3/2012 | Kelly et al. ......... A61B 17/064 514/772.7 |
| 2015/0038793 | A1 | 2/2015 | Prior et al. |
| 2015/0305738 | A1 | 10/2015 | Thomas |
| 2017/0281154 | A1 | 10/2017 | Hess et al. |

OTHER PUBLICATIONS

U.S. Appl. No. 15/637,702, filed Jun. 29, 2017.
U.S. Appl. No. 15/637,683, filed Jun. 29, 2017.
U.S. Appl. No. 15/637,688, filed Jun. 29, 2017.
U.S. Appl. No. 15/637,712, filed Jun. 29, 2017.
U.S. Appl. No. 15/637,696, filed Jun. 29, 2017.
U.S. Appl. No. 15/637,707, filed Jun. 29, 2017.
U.S. Appl. No. 15/637,778, filed Jun. 29, 2017.
European Search Report, Extended, and Written Opinion dated Aug. 28, 2018 for Application No. EP 18180443.6, 8 pgs.
International Search Report and Written Opinion dated Aug. 16, 2018 for Application No. PCT/IB2018/054437, 15 pgs.

\* cited by examiner

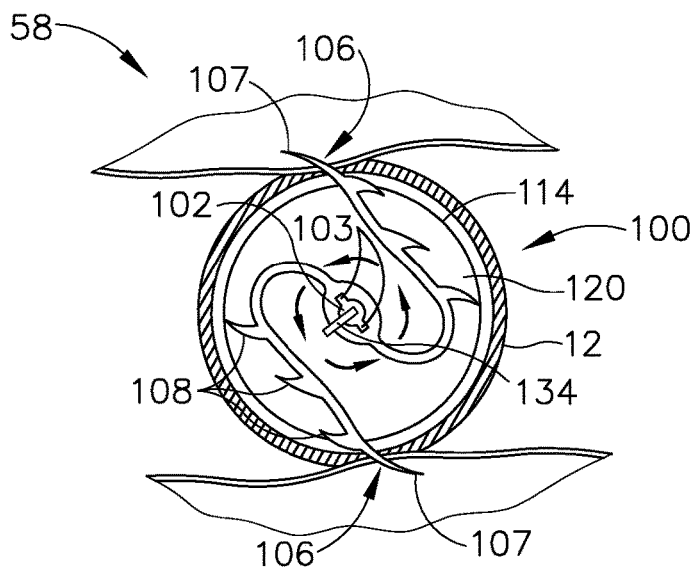
Fig.11A
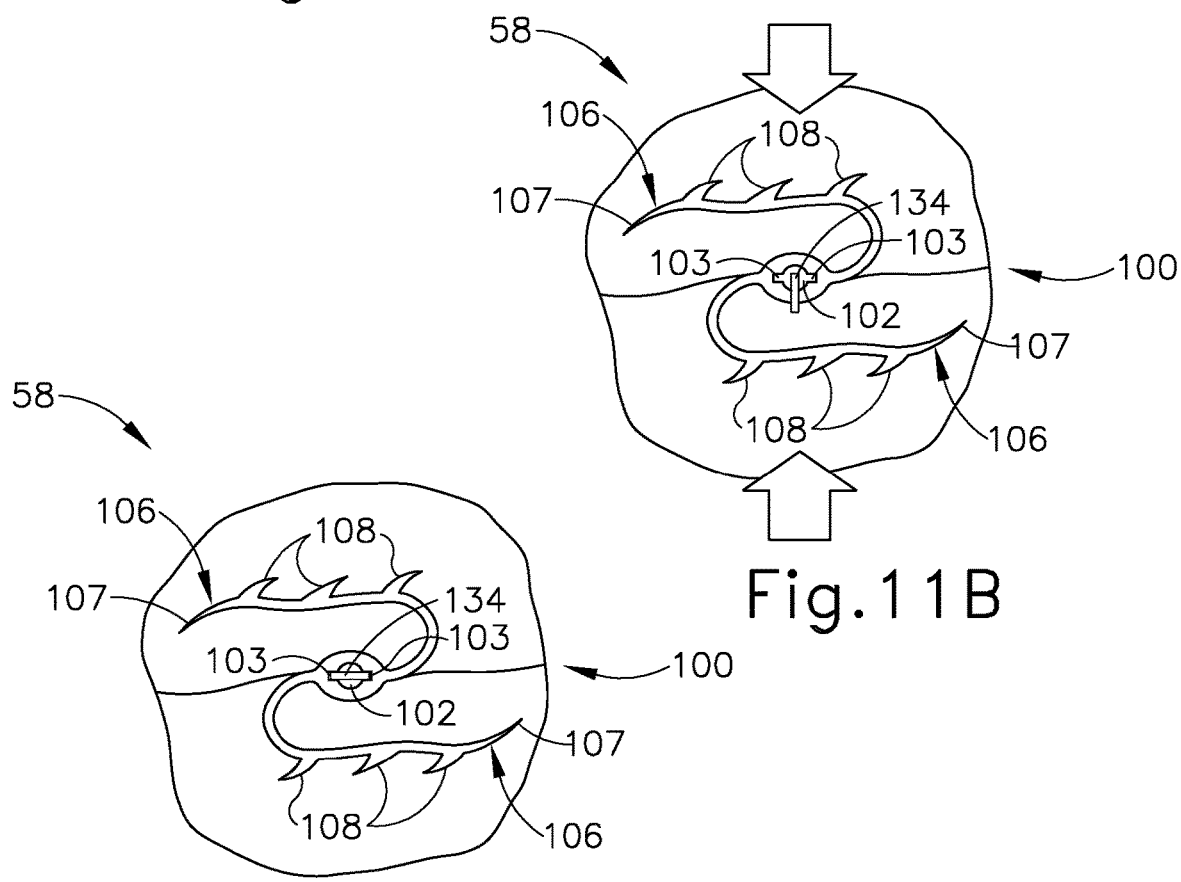
Fig.11B
Fig.11C

TROCAR OBTURATOR WITH DETACHABLE ROTARY TISSUE FASTENER

BACKGROUND

Surgical procedures may require a clinician to gain access to a cavity or other desirable surgical site within a body of a patient. To perform such a surgical procedure, an incision may be made through a tissue of the patient into the cavity. Some conventional surgical procedures may apply a knife, such as a scalpel, to the tissue for the incision, while some less invasive surgical procedures, such as laparoscopic and endoscopic surgical procedures, may access the cavity through a trocar assembly. Trocar assemblies generally include a trocar obturator received within a trocar cannula. In use, the clinician directs the trocar obturator and the cannula through the tissue in order to access the cavity of the desirable surgical site. Once accessed, the clinician withdraws the trocar obturator from the trocar cannula so that the trocar cannula may be used to introduce surgical instruments into the cavity for treatment.

Merely exemplary trocar assemblies, components thereof, and other varieties of wound closure devices are provided for in U.S. Pat. No. 7,981,092, entitled "Vibratory Trocar," issued Jul. 19, 2011; U.S. Pat. No. 8,226,553, entitled "Access Device with Insert," issued on Jul. 24, 2012; U.S. Pat. No. 8,251,900, entitled "Surgical Access Devices and Methods Providing Seal Movement in Predefined Paths," issued on Aug. 28, 2012; U.S. Pat. No. 8,579,807, entitled "Absorbing Fluids in a Surgical Access Device," issued on Nov. 12, 2013; U.S. Pat. No. 8,568,362, entitled "Surgical Access Device with Sorbents," issued on Oct. 29, 2013; U.S. Pat. No. 8,636,686, entitled "Surgical Access Device," issued on Jan. 28, 2014; U.S. Pat. No. 8,690,831, entitled "Gas Jet Fluid Removal in a Trocar," issued on Apr. 8, 2014; U.S. Pat. Pub. No. 2008/0200950, entitled "Surgical Hook," published on Aug. 21, 2008, now abandoned; U.S. Pat. Pub. No. 2015/0038793, entitled "Devices, Systems, and Methods for Providing Surgical Access and Facilitating Closure of Surgical Access Openings," published on Feb. 5, 2015, issued as U.S. Pat. No. 10,258,324 on Apr. 16, 2019; U.S. Pat Pub. No. 2015/0038994, entitled "Devices, Systems, and Methods for Providing Surgical Access and Facilitating Closure of Surgical Access Openings," published on Feb. 5, 2015, issued as U.S. Pat. No. 9,700,303 on Jul. 11, 2017; and U.S. Pat. Pub. No. 2015/0094741, entitled "Wound Closure Device including Mesh Barrier." Published on Apr. 2, 2015, issued as U.S. Pat. No. 9,687,226 on Jun. 27, 2017. The disclosure of each of the above-cited U.S. Patents and Publications is incorporated by reference herein.

Surgical instruments for use with such trocars may have a distal end effector for engaging tissue through the trocar cannula in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Laparoscopic and endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the cavity of the patient. Positioning of an end effector may be further facilitated through inclusion of one or more articulation joints or features, enabling the end effector to be selectively articulated or otherwise deflected relative to the longitudinal axis of the shaft.

While various kinds of surgical instruments, including trocar assemblies and end effectors, and other associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 11A depicts a distal end plan view of the tissue fastener of FIG. 5, taken along a centerline thereof, with the tissue fastener inserted into the tissue opening for suturing the opening closed, and an internal hook in a locked position;

FIG. 11B depicts the distal end plan view of the tissue fastener similar to FIG. 11A, but with the tissue fastener rotatably driven against the tissue to fully close the opening;

FIG. 11C depicts the distal end plan view of the tissue fastener similar to FIG. 11B, but with the tissue fastener securely fastened to the tissue to close the opening and the internal hook in an unlocked position;

Figure 1:
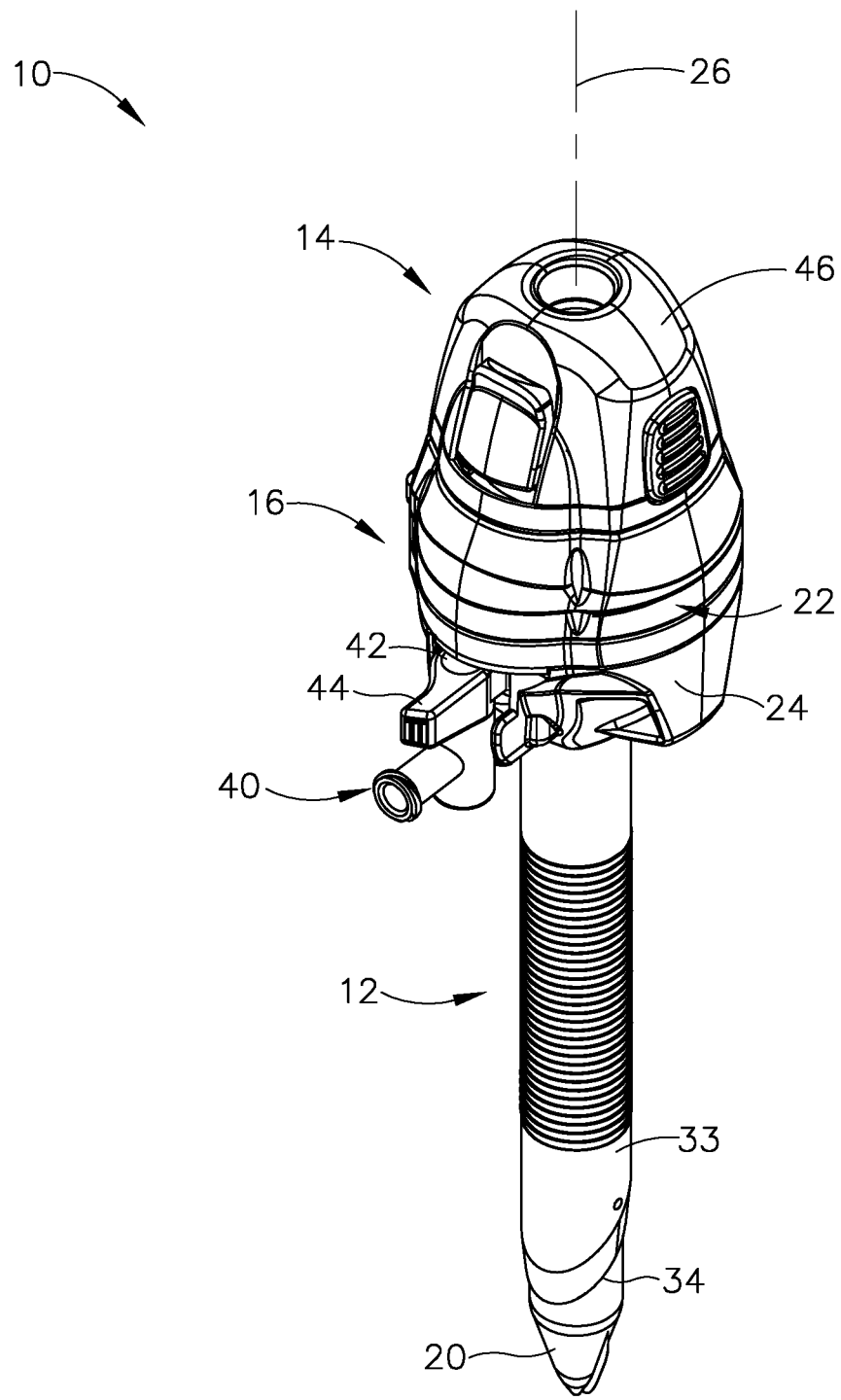
FIG. 1 depicts a perspective view of an exemplary trocar assembly.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Access Device

Figure 2:
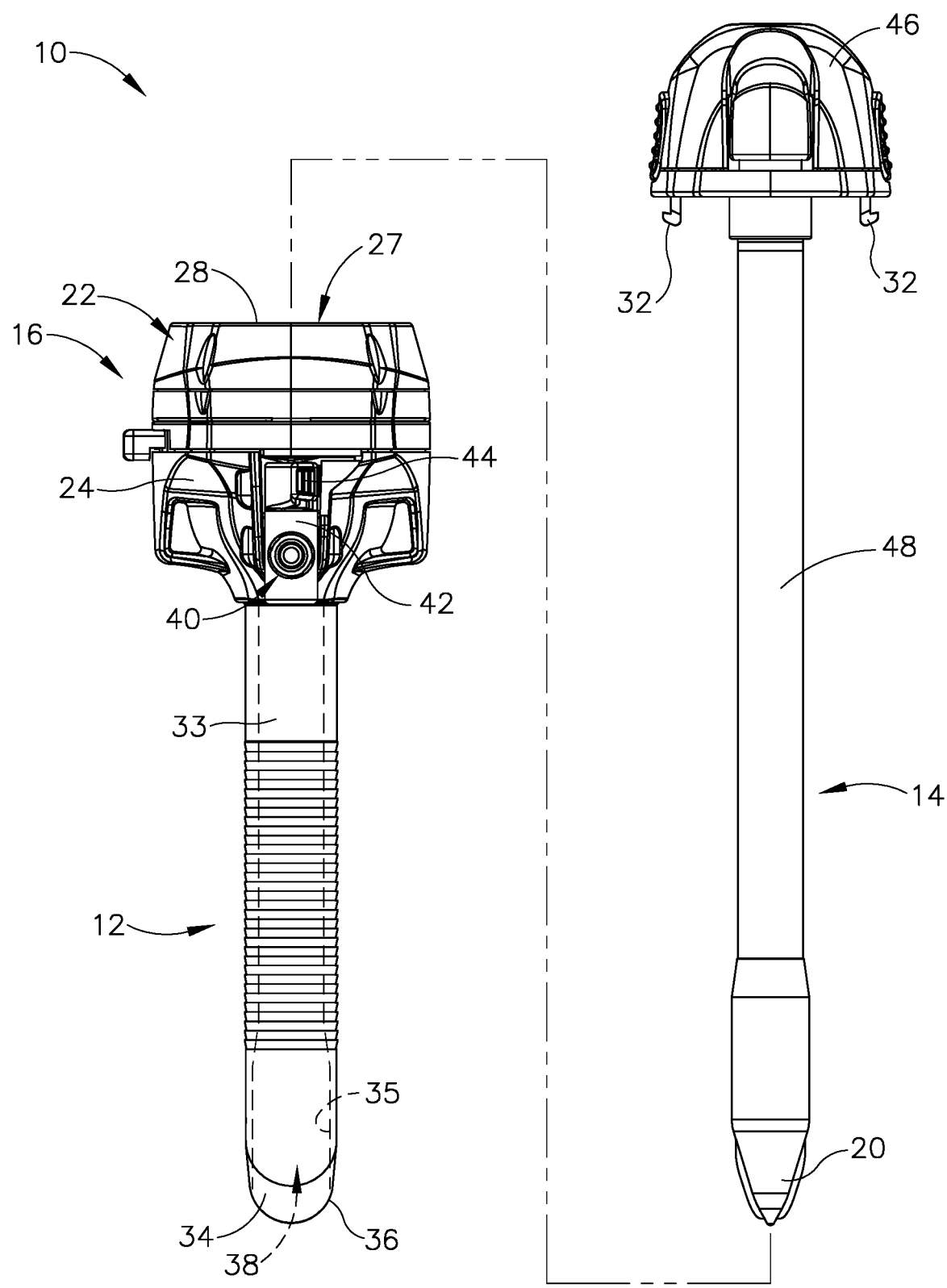
FIG. 2 depicts a partially exploded side elevational view of the trocar assembly of FIG. 1 having a trocar housing, a trocar cannula, and an obturator.

FIGS. 1-2 depict an exemplary surgical access device in the form of a first exemplary trocar assembly (10) that includes a trocar cannula (12) and a trocar obturator (14). Trocar obturator (14) is removably received within trocar cannula (12) through a trocar housing (16) of trocar cannula (12). As shown in FIG. 1 with trocar obturator (14) positioned within trocar cannula (12), a clinician inserts trocar assembly (10) through tissue (17) (see FIG. 3A) of a patient at a desirable surgical site for accessing a cavity (18) (see FIG. 3A) within the patient. By way of example only, trocar assembly (10) may be inserted in a patient's abdomen, between two of the patient's ribs, or elsewhere. A tip (20) of trocar obturator (14) projects distally from trocar cannula (12) to puncture tissue (17) (see FIG. 3A) for introducing a distal end portion of trocar cannula (12) into cavity (18) (see FIG. 3B). The clinician proximally withdraws trocar obturator (14) from trocar cannula (12) such that cavity (18) (see FIG. 3C) within the patient is in communication with a surgical environment via trocar cannula (12). The clinician may then introduce a fluid, such as a gas, through trocar cannula (12) for inflating cavity (18) (see FIG. 3A) and/or an end effector of a surgical instrument through trocar cannula (12) for engaging tissue (17) to achieve a diagnostic or therapeutic effect.

It should be understood that terms such as "proximal" and "distal" are used herein with reference to the clinician gripping trocar housing (16). Thus, tip (20) is distal with respect to the more proximal trocar housing (16). It will be further appreciated that for convenience and clarity, spatial terms such as "vertical" and "horizontal" are used herein with respect to the drawings. However, surgical instruments are used in many orientations and positions, and these terms are not intended to be limiting and absolute. Further, in some instances, components are referred to interchangeably with and without the term "assembly," e.g., a trocar and a trocar assembly. There is no particular intention for the terms to refer to different components. Likewise, terms such as "instrument" and "device" may be used interchangeably.

A. Exemplary Trocar Assembly with Cannula and Obturator

Trocar assembly (10) of FIGS. 1-2 includes cannula (12) extending distally from trocar housing (16). In the present example, trocar housing (16) has a generally cylindrical shape with a proximal removable cap (22) atop a distal housing chamber (not shown). Cap (22) is selectively attachable and detachable from housing chamber (not shown). Trocar housing (16) includes a housing sidewall (24) that extends circumferentially around a central longitudinal axis (26) through trocar assembly (10), and thus along trocar cannula (12). Trocar housing (16) further includes a central lumen (27) extending from a proximal housing end opening (28) to a distal housing end opening (not shown). As shown, cap (22) selectively mates with housing sidewall (24) via distal mating members (not shown) and further includes proximal mating members, such as slots (not shown), configured to removably connect to a pair of tabs (32), respectively, that extend distally from a portion of obturator (14). However, it will be appreciated that alternative structures and devices may also be removably connected to cap (22) during use.

Cannula (12) extends distally from trocar housing (16), and is also generally defined by a cannula sidewall (33) extending circumferentially around central longitudinal axis (26). Cannula sidewall (33) extends distally to a beveled end (34) such that cannula sidewall (33) and beveled end (34) are configured to be inserted through tissue (17) (see FIG. 3A) as discussed below in greater detail for accessing cavity (18) (see FIG. 3A). To this end, cannula (12) generally has a smaller diameter than trocar housing (16), which is configured to remain exterior of tissue (17) (see FIG. 3C). In addition, cannula (12) defines an interior lumen (35) with a proximal cannula end opening (not shown) and a cannula distal end opening (36), which extends through beveled end (34). In the present example, distal housing end opening (not shown) of trocar housing (16) fluidly connects to proximal cannula end opening (not shown) such that central lumen (27) of trocar housing (16) and interior lumen (35) of cannula (12) define a working channel (38). Working channel (38) thus extends from proximal housing end opening (28) to cannula distal end opening (36) and is configured to receive one or more surgical instruments therethrough for accessing cavity (18).

Furthermore, an insufflation port (40) is operatively connected to trocar housing (16) to control the flow of an insufflation fluid, such as carbon dioxide, through a portion of cannula (12) and into cavity (18). More particularly, insufflation port (40) includes a stopcock valve (42) and a cock valve lever (44), which can work together to allow and/or prevent passage of the insufflation fluid into tubing (not shown), through trocar housing (16), and into trocar cannula (12). Trocar housing (16) and cannula (12) respectively have proximal and distal seal assemblies (not shown) positioned within central lumen (27) and interior lumen (35) of working channel (38). In the present example, the proximal seal assembly is an instrument seal (not shown), whereas the distal seal assembly (not shown) is a zero-closure seal, such as a duckbill seal (not shown). Instrument seal (not shown) is retained with cap (22) and configured to fluidly seal against a surgical instrument extending through working channel (38). In contrast, duckbill seal (not shown) is configured to form a seal in working channel (38) when no instrument is disposed therethrough to thereby inhibit the leakage of insufflation fluid during use. Of course, it will be appreciated that alternative seal assemblies may be positioned within working channel (38) for inhibiting such leakage of insufflation fluid.

As discussed briefly above, obturator (14) is used in conjunction with cannula (12) for inserting trocar assembly (10) into the patient. Obturator (14) of the present example, includes a handle head (46) with a cylindrical shaft (48) extending distally therefrom to tip (20), which is generally configured to puncture tissue (17) (see FIG. 3A) as described below in greater detail. Handle head (46) is configured to be gripped by the clinician during use and includes selectively movable tabs (32) extending distally to removably connect with trocar housing (16) for selective securement. Shaft (48) is received through working channel (38) such that tip (20) extends distally from beveled end (34). Of course, obturator (14) may be selectively removed from cannula (12) and trocar housing (16) to free working channel (38) for use. While the present example of trocar assembly (10) has obturator (14), it will be appreciated that cannula (12) may be inserted in some examples without obturator (14) or may be alternatively configured to aid insertion without using obturator (14).

B. Exemplary Method of Accessing a Cavity within a Patient

Figure 3A:
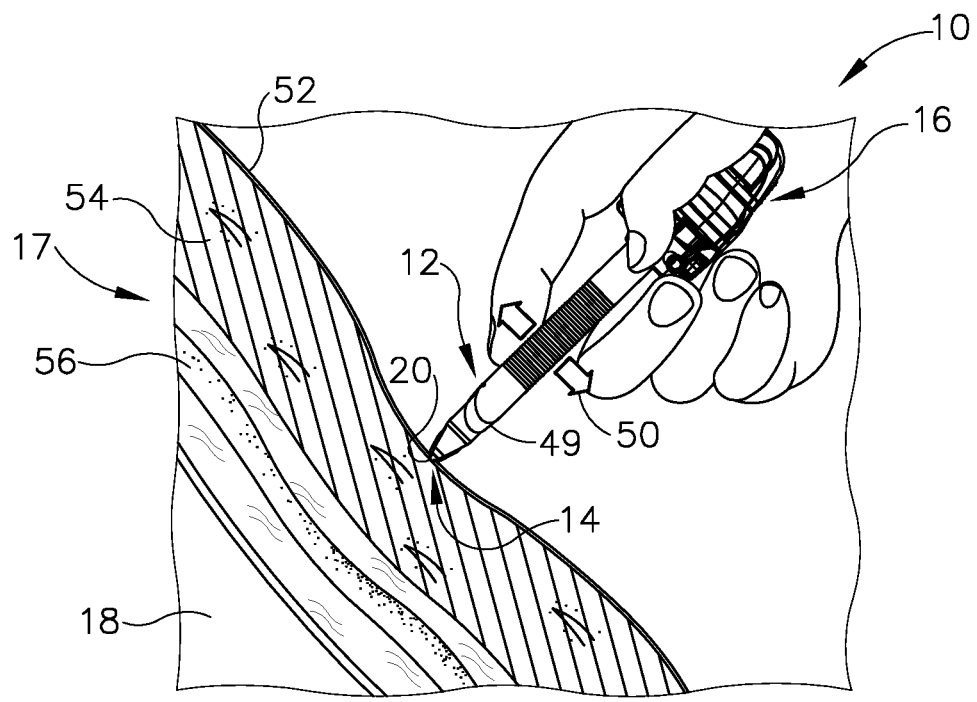
FIG. 3A depicts a sectional side view of tissue of a patient with the trocar assembly of FIG. 1 being manipulated by a clinician through the tissue.
Figure 3B:
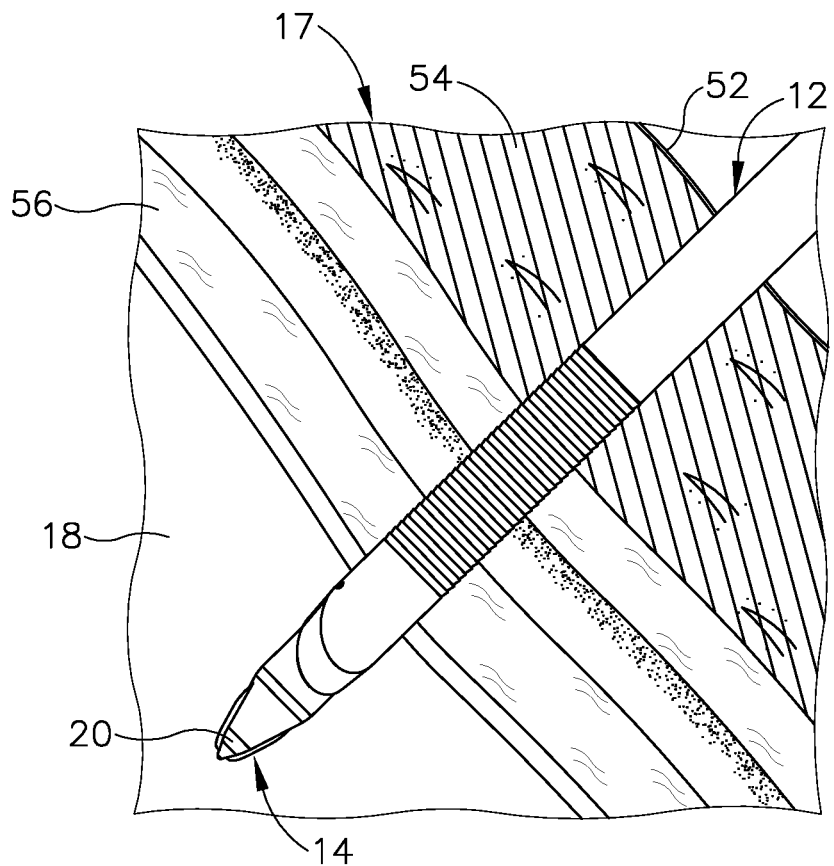
FIG. 3B depicts a sectional side view of the tissue and trocar assembly of FIG. 3A, with the trocar assembly of FIG. 1 inserted through the tissue and received within a cavity of the patient.
Figure 3C:
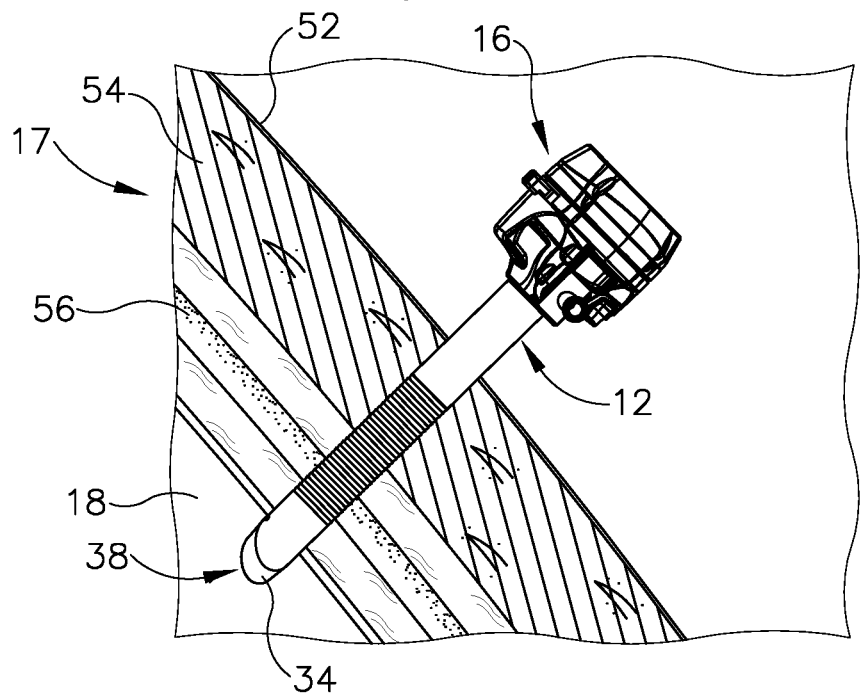
FIG. 3C depicts a sectional side view of the tissue and the trocar assembly of FIG. 3A, with the obturator withdrawn from the trocar cannula for accessing the cavity via a working channel through the trocar cannula and the trocar housing.
Figure 3D:
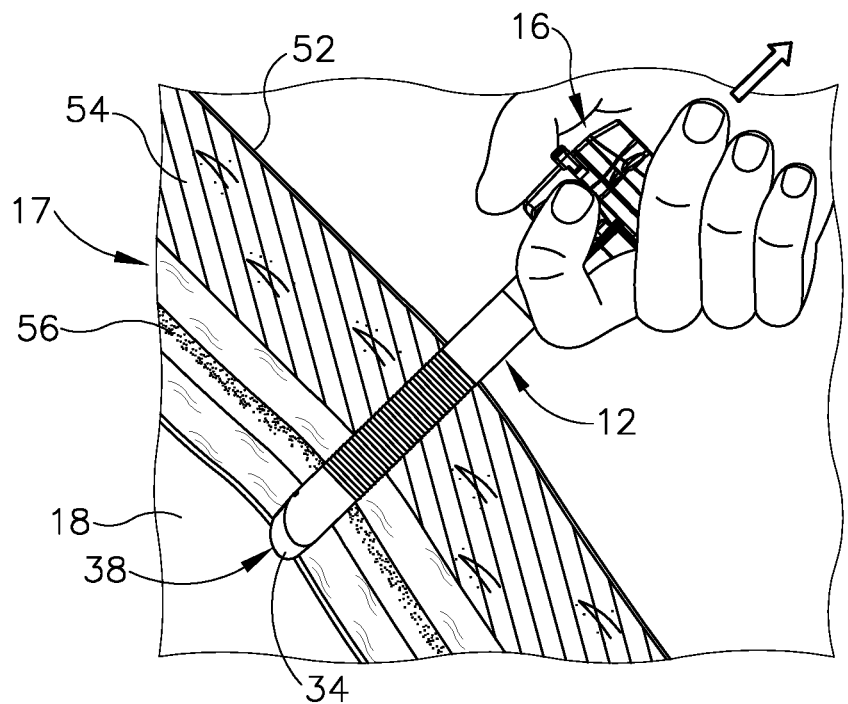
FIG. 3D depicts a sectional side view of the tissue and the trocar assembly of FIG. 3C, with the trocar housing and the trocar cannula being removed from the cavity and the tissue of the patient.

FIGS. 3A-3D illustrate accessing cavity (18) through tissue (17) with trocar assembly (10) discussed above. Tissue (17) of the present example more particularly has relatively outward superficial layers and relatively inward deep layers. Superficial layers generally include an outer layer of skin (52) and an inner layer of fat (54); whereas the deeper layers include layers of fascia (56), which are fibrous and flexible with relatively higher tensile strength than the superficial layers. As shown in FIG. 3A, with obturator (14) received within cannula (12) and connected to trocar housing (16), the clinician manipulates trocar assembly (10) to urge tip (20) of obturator (14) against skin (52) and inward toward cavity (18) while rotating trocar assembly (10) back and forth. Arrow (49) and arrow (50) respectively indicate this inward and rotatable movement. Continued inward urging of trocar assembly (10) further directs tip (20) and beveled end (34) of cannula (12) through the layers of fat (54) and fascia (56) and into cavity (18) as shown in FIG. 3B. The clinician then disconnects obturator (14) from trocar housing (16) and withdraws obturator (14) from cannula (12) to establish access from the exterior of tissue (17) into cavity (18) via working channel (38) as shown in FIG. 3C for achieving a diagnostic or therapeutic effect with another surgical instrument (not shown). Once the diagnostic or therapeutic effect is complete, clinician withdraws cannula (12) and trocar housing (16) outwardly for removal from tissue (17) as shown in FIG. 3D.

Figure 4A:
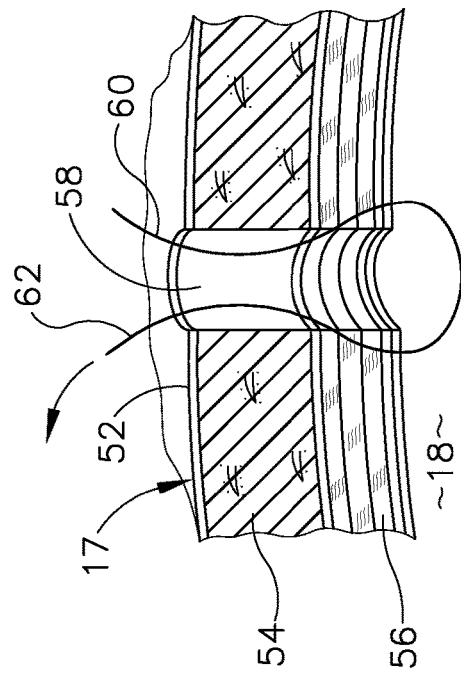
FIG. 4A depicts another sectional side view of the tissue shown in FIGS. 3A-3D following removal of the trocar assembly of FIG. 1, with an opening through the tissue and a suture thread being introduced into a portion of the tissue for suturing the opening closed.
Figure 4B:
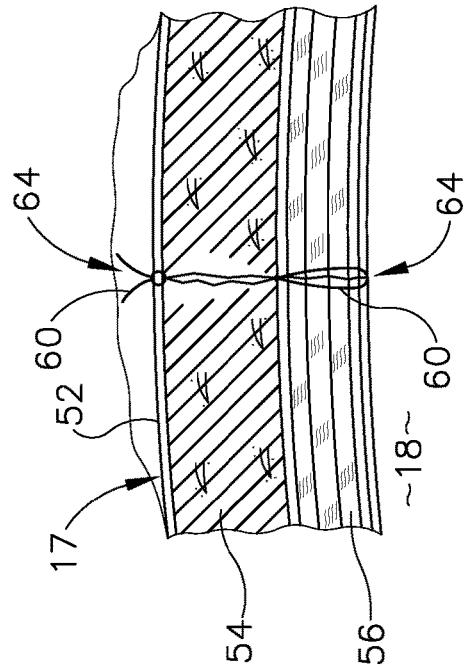
FIG. 4B depicts a sectional side view of the tissue of FIG. 4A, with the suture thread being introduced though another portion of the tissue and pulled through the tissue.
Figure 4C:
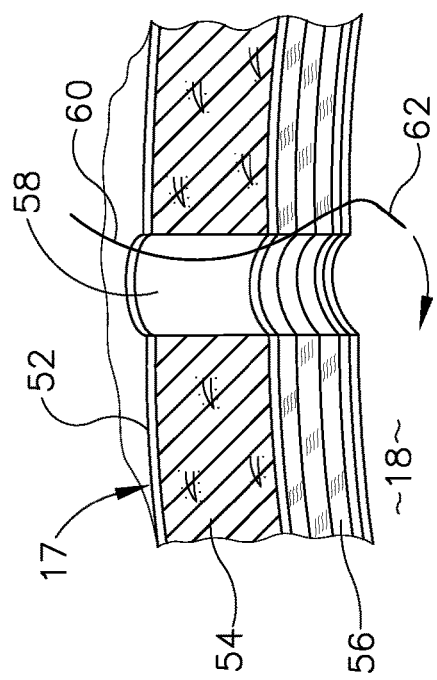
FIG. 4C depicts a sectional side view of the tissue of FIG. 4A, with the suture thread tightened and knotted for at least partially closing the opening.
Figure 4D:
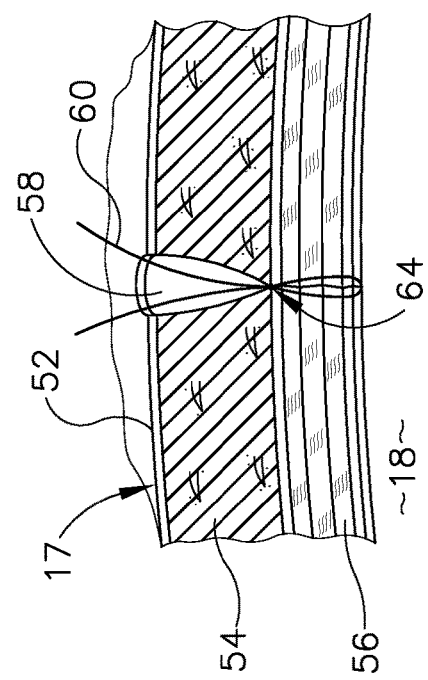
FIG. 4D depicts a sectional side view of the tissue of FIG. 4A, with additional suturing for further closing the opening.

As shown in FIG. 4A, removal of cannula (12) from tissue (17) generally results in a tissue opening (58), which may also be referred to as a tissue port or tissue wound, that clinician closes to encourage healing of tissue (17). While some tissue openings may sufficiently close as tissue (17) comes together, other openings, such as tissue opening (58), are sutured closed with a suture thread (60). In one example shown in FIGS. 4A-4D, suture thread (60) is removably coupled with a needle (62) for guiding suture thread (62) through tissue (17) as the clinician manipulates needle (62). More particularly, as shown in FIG. 4B, the clinician directs needle (62) downwardly through fascia (56) on one side of tissue opening (58) and then upwardly through fascia (56) on the other side of tissue opening (58) as needle (62) clears tissue (17). Notably, the clinician threads needle (62) though fascia (56) a desirable distance from tissue opening (58) to provide a relatively close proximity to tissue opening (58); but also at a sufficient distance to provide ample fascia (56) for anchoring suture thread (60) therein. As shown in FIG. 4C, suture thread (60) from respective sides of tissue opening (58) are brought together and pulled to similarly pull tissue (17) together and at least partially close tissue opening (58). The clinician then knots suture thread (60) to secure tissue (17) together and sufficiently close tissue opening (58) with a formed suture (64) as shown in FIG. 4D. Additional sutures (64) may be placed along tissue (17) to further close tissue opening (58) and encourage healing of tissue (17).

While the above described suturing technique shown in FIGS. 4A-4D is one exemplary procedure for closing tissue opening (58) with suture thread (60) following use of trocar assembly (10) (see FIG. 1), other exemplary procedures and devices may be alternatively used for closing such tissue openings. By way of example, U.S. patent application Ser. No. 15/088,723, entitled "Surgical Access Devices with Integrated Wound Closure Features," filed on Apr. 2, 2016, issued as U.S. Pat. No. 10,299,785 on May 28, 2019, which is incorporated by reference herein in its entirety, describes an alternative trocar assembly and suturing technique. To this end, alternative trocar assemblies and suturing techniques may be used in any combination as desired by the clinician.

II. Exemplary Trocar Assembly with Detachable Tissue Fastener

In some instances, inserting and pulling suture thread (60) through multiple portions of tissue opening (18) may be difficult, labor intensive, and/or time consuming. It may be thus be beneficial in such instances to close tissue opening (58) with an alternative suture prior to the removal of trocar assembly (10). For example, an alternative obturator (114), like obturator (14) discussed above, includes a suture (100), which may also be referred to herein as a tissue fastener (100), that is preassembled and releasably connected to obturator (14) for closing tissue opening (18).

The following description provides various examples of a trocar assembly (110) including various exemplary obturators (114, 214) with respective tissue fasteners (100, 200) releasably secured thereto. As will be described in greater detail below, each tissue fastener (100, 200) is configured to close tissue opening (58) by rotatably driving obturator (114, 214) within tissue opening (58) and then releasing tissue fastener (100, 200) for closure of tissue (17) and removal of obturator (114, 214). Tissue fasteners (100, 200) described below may be used with any obturator (12) and corresponding trocar assembly (10, 110) described above and below and in any of the various procedures described in the various patent references cited herein. To this end, like numbers below indicate like features described above. Other suitable ways in which various trocar assemblies may be used will be apparent to those of ordinary skill in the art in view of the teachings herein.

A. First Securement Mechanism with a Detachable Tissue Fastener

Figure 5:
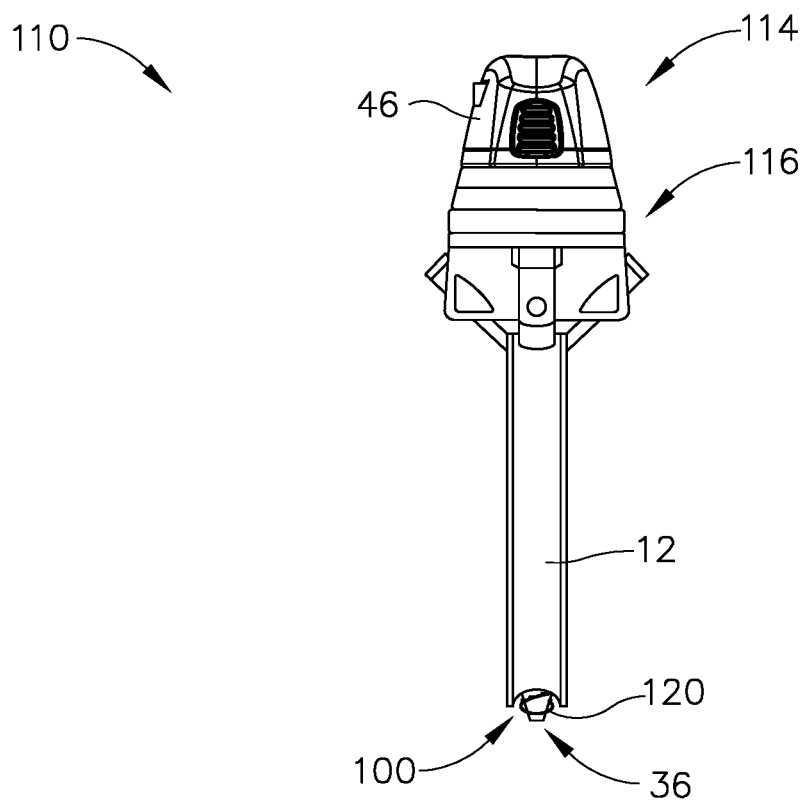
FIG. 5 depicts a side elevational view of an exemplary alternative trocar assembly with a tissue fastener attached to an obturator via a first securement mechanism.
Figure 6:
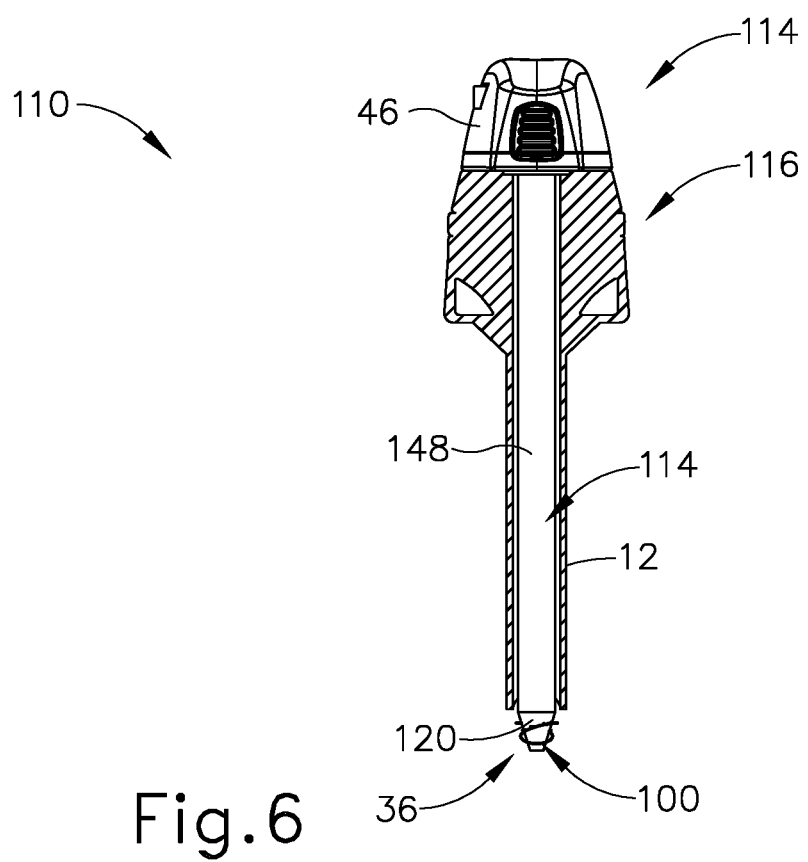
FIG. 6 depicts a cross-sectional side view of the trocar assembly of FIG. 5, taken along a centerline thereof.

FIGS. 5-6 show a trocar assembly (110) including trocar cannula (12) and an exemplary alternative trocar obturator (114). Like obturator (14) (see FIG. 1), trocar obturator (114) is removably received within trocar cannula (12) through trocar housing (16). Trocar obturator (114) includes a tissue fastener (100), a distal tip (120) and a cylindrical shaft (148). Distal tip (120) is positioned at a distal end of cylindrical shaft (148). Tissue fastener (100) is releasably attached to trocar obturator (114) at distal tip (120). Distal tip (120) is substantially positioned within trocar cannula (12) at cannula distal end opening (36) when trocar obturator (114) is initially positioned within trocar cannula (12). Cylindrical shaft (148) of trocar obturator (114) is configured to translate distally within trocar cannula (12) to allow distal tip (120) to extend beyond cannula distal end opening (36) and thereby substantially expose tissue fastener (100) from trocar cannula (12).

Figure 7:
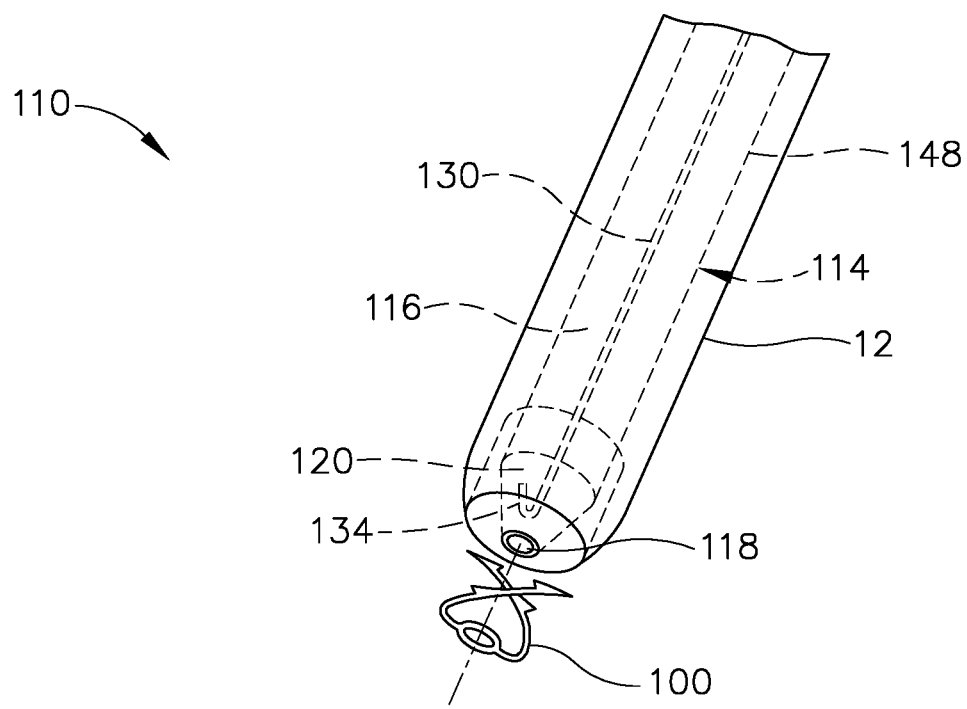
FIG. 7 depicts a partially exploded view of the trocar assembly of FIG. 5, with the tissue fastener detached from the obturator.

As shown in FIGS. 6-7, cylindrical shaft (148) defines an internal channel (116) with a longitudinal length that terminates on a distal end at a shaft opening (118) and on a proximal end at handle head (46). Shaft opening (118) is centered on distal tip (120) and provides communication between internal channel (116) and the external surroundings of distal tip (120). Trocar obturator (114) further includes a first securement mechanism (130) extending within and along the longitudinal length of internal channel (116). Securement mechanism (130) terminates on a distal end at a hook member (134) and on a proximal end at a handle (not shown). Hook member (134) is configured to releasably engage distal tip (120) at shaft opening (118). Handle (not shown) is positioned adjacent to handle head (46) and is configured to slidably translate securement mechanism (130) within inner channel (116). Handle (not shown) is further configured to actuate hook member (134) from a locked position (see FIGS. 10A-10B) to an unlocked position (see FIG. 10C) to thereby allow hook member (134) to engage and disengage distal tip (120) of trocar obturator (114) for releasing tissue fastener (100) as discussed below in greater detail.

Figure 8:
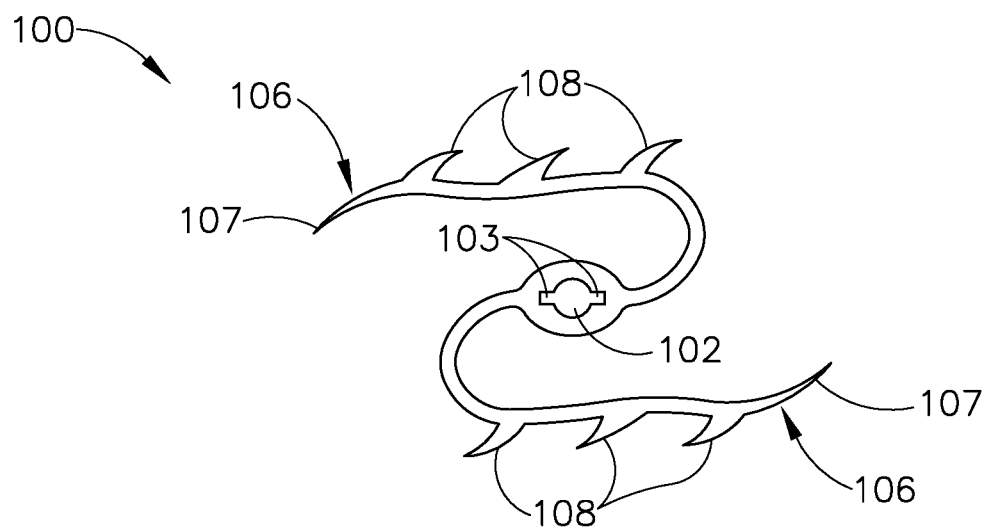
FIG. 8 depicts a distal end plan view of the tissue fastener of FIG. 5.
Figure 9:
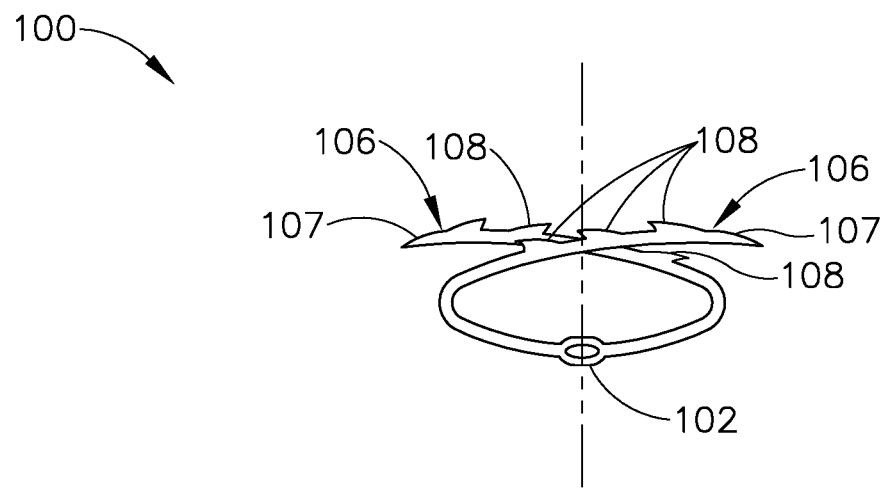
FIG. 9 depicts a side elevational view of the tissue fastener of FIG. 5.

As seen in FIG. 8, tissue fastener (100) includes a base (102) and a pair of arms (106) extending outwardly therefrom. In the present example, tissue fastener (100) is formed of an absorbable material configured to dissolve for absorption within the patient after a predetermined lapse of exposure to the tissue portions of tissue opening (58). As a merely illustrative example, tissue fastener (100) is formed of an absorbable polymer material. Arms (106) are integrally formed with base (102) and extend longitudinally and angularly outwardly from base (102). As shown in FIGS. 8-9, arms (106) extend along respective helical paths. Base (102) is configured to be received against distal tip (120). Base (102) has a diameter that is substantially equivalent to shaft opening (118) and includes a slot (103) that is configured to receive hook member (134) to thereby allow securement mechanism (130) to releasably attach tissue fastener (100) to distal tip (120) through shaft opening (118). Although not shown, it will be apparent to those of ordinary skill in the art that tissue fastener (100) may include more or fewer arms (106) extending from base (102).

Each arm (106) terminates in a piercing tip (107) that is configured to pierce and penetrate tissue. Each arm (106) also includes a plurality of barbs (108) extending outwardly therefrom. Although three barbs (108) are shown extending from arms (106), it should be understood that more or fewer barbs (108) may be included on arms (106). Barbs (108) are configured to securely fix arms (106) to tissue portions of tissue opening (58) as tissue fastener (100) is rotatably driven within tissue opening (58) at a predetermined rotatable-release force. Arms (106) are configured to draw the tissue portions of tissue opening (58) together upon rotation of distal tip (120) and tissue fastener (100) within tissue opening (58). Each barb (108) of the present example extends at an obtuse angle relative piercing tip (107) on each respective arm (106) such that arms (106) insert into tissue with relative ease. However, upon removal forces, barbs (108) catch the tissue for securement of arms (106) in the tissue. Thus, while barbs (108) are configured to permit arms (106) to be driven into tissue in a first respective direction, barbs (108) are configured to prevent arms (106) from being pulled from the tissue in a second respective direction after arms (106) are driven into the tissue. In the present example, arms (106) are sufficiently rigid for penetrating the tissue; but are configured to deflect upon application of excessive force.

Figure 10A:
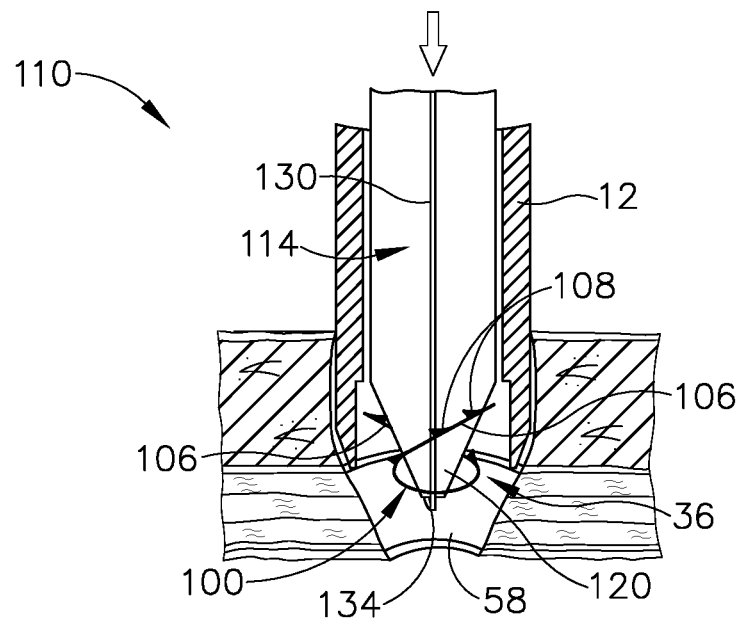
FIG. 10A depicts a partial cross-sectional side view of the trocar assembly of FIG. 5, taken along a centerline thereof, with the obturator in a retracted position and adjacent to a tissue opening.

FIGS. 9-10A illustrate the helical shape of tissue fastener (100) through the outward and angular extension of arms (106) from base (102) such that arms (106) lie in varying dimensional planes from each other. The helical shape of tissue fastener (100) is configured to allow arms (106) to coil around distal tip (120) of trocar obturator (114); and to allow arms (106) to be rotatably driven into tissue like a corkscrew. Tissue fastener (100) is releasably attached to distal tip (120) through the engagement of hook member (134) and base (102) at shaft opening (118). More particularly, base (102) is releasably captured between hook member (134) and distal tip (120). Thus, upon disengaging hook member (134) from base (102), tissue fastener (100) is released from trocar obturator (114).

In the present example, after a clinician inserts trocar assembly (110) through tissue (17) of a patient and achieves the diagnostic or therapeutic effect desired within cavity (18), the clinician slightly withdraws trocar cannula (12) and inserts trocar obturator (114) within trocar cannula (12) rather than removing trocar assembly (110) from tissue opening (58). At this stage, as shown in FIG. 10A, cannula distal end opening (36) is just proximal to the distal surface of the tissue defining tissue opening (58) (e.g., adjacent to one or more of the innermost layers of the fascia of the patient). As also seen in FIG. 10A, while trocar obturator (114) is positioned within trocar cannula (12), distal tip (120) is positioned adjacent cannula distal end opening (36). Distal tip (120) is configured to project distally from cannula distal end opening (36) when trocar obturator (114) is translated distally within trocar cannula (12).

Figure 10B:
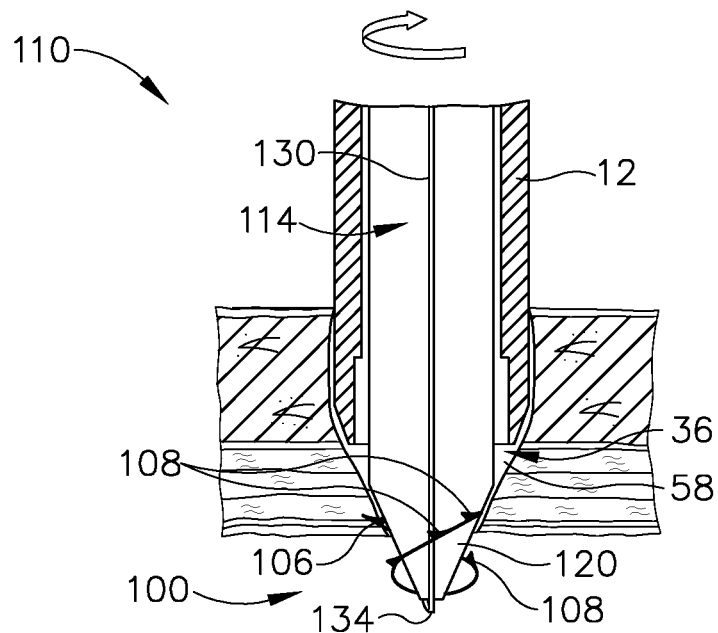
FIG. 10B depicts the partial cross-sectional side view of the trocar assembly similar to FIG. 10A, but with the obturator advanced into the tissue opening and the tissue fastener rotatably driven against the tissue to suture the opening closed.
Figure 10C:
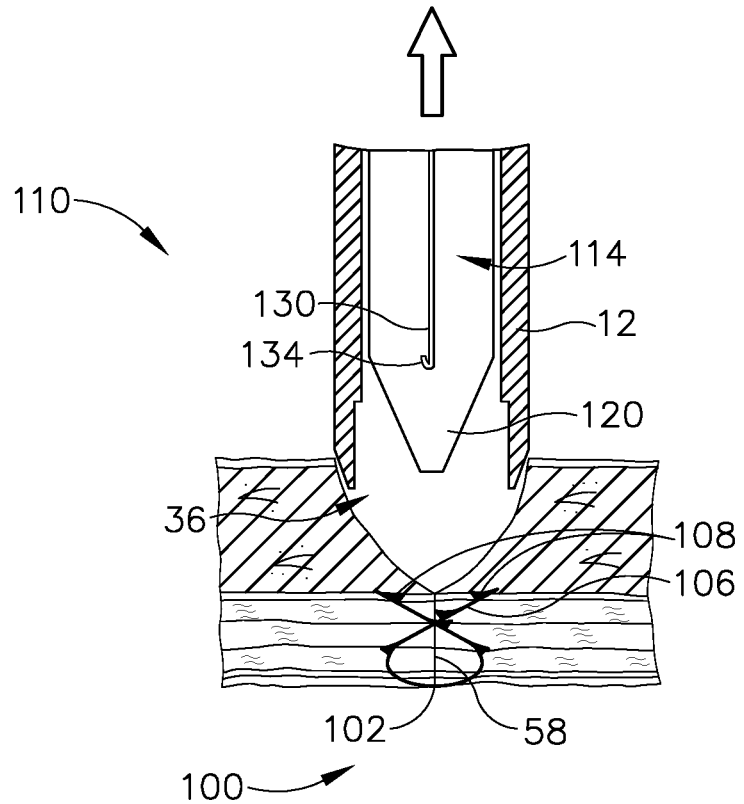
FIG. 10C depicts the partial cross-sectional side view of the trocar assembly similar to FIG. 10B, but with the obturator retracted from the tissue opening and the tissue fastener detached from the obturator and securely fastened to the tissue.

Once trocar obturator (114) is distally advanced within trocar cannula (12) to an extent where distal tip (120) is positioned beyond cannula end opening (36), as seen in FIG. 10B, tissue fastener (100) contacts tissue portions of tissue opening (58). In this instance, as further seen in FIG. 11A, arms (106) press against the tissue portions of tissue opening (58). The clinician then rotates trocar obturator (114) within trocar cannula (12) with sufficient force for arms (106) to pierce the tissue and cause barbs (108) to catch the tissue portions of tissue opening (58). As seen in FIGS. 10C and 11B, rotating trocar obturator (114) and distal tip (120) allows tissue fastener (100) to draw the tissue portions of tissue opening (58) together to partially close tissue opening (58) as arms (106) embed in the tissue. In the present example, tissue opening (58) is "partially closed" in the sense that the region of the region of tissue opening (58) at the fascia (56) is closed but not the region of tissue opening (58) that is proximal to the fascia (56).

With tissue opening (58) partially closed, the clinician disengages securement mechanism (130) from distal tip (120) and retracts trocar obturator (114) proximally through trocar cannula (12). More particularly, as best seen in FIG. 10C and FIG. 11C, securement mechanism (130) is rotated with handle (not shown) to align hook member (134) with slot (103) of base (102). With hook member (134) aligned with slot (103) and disengaged from base (102), handle (not shown) is translated proximally to thereby pull securement mechanism (130) proximally. With hook member (134) in the unlocked position, hook member (134) releases tissue fastener (100) from distal tip (120). In this instance, retracting trocar obturator (114) allows tissue fastener (100) to maintain its secured position in closing tissue opening (58) at fascia (56). After fastener (100) is used to close fascia (56) and trocar assembly (110) is fully removed from the patient, skin (52) may be secured to close the proximal end of tissue opening (58) using conventional suture, stapling, adhesive, and/or any other suitable devices or techniques.

In versions where fastener (100) is formed of a bioabsorbable material, after tissue fastener (100) has been securely attached to tissue opening (58) (e.g., in the innermost layer(s) of fascia (56) tissue), tissue fastener (100) is eventually absorbed by the tissue and thus effectively dissolves in the patient's body after the predetermined lapse of exposure. In the present example, the material forming tissue fastener (100) does not degrade until the tissue associated with tissue opening (58) has scarred or otherwise healed to the point where tissue fastener (100) is no longer needed to hold tissue opening (58) closed.

B. Second Securement Mechanism with a Detachable Tissue Fastener

Figure 12A:
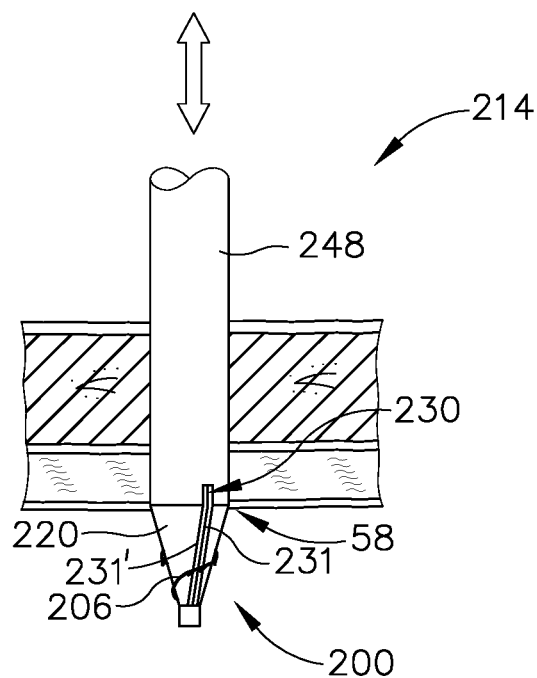
FIG. 12A depicts a partial side elevational view of another exemplary alternative trocar assembly with an obturator including a second securement mechanism, with a securement slot and the tissue fastener attached thereon.
Figure 12B:
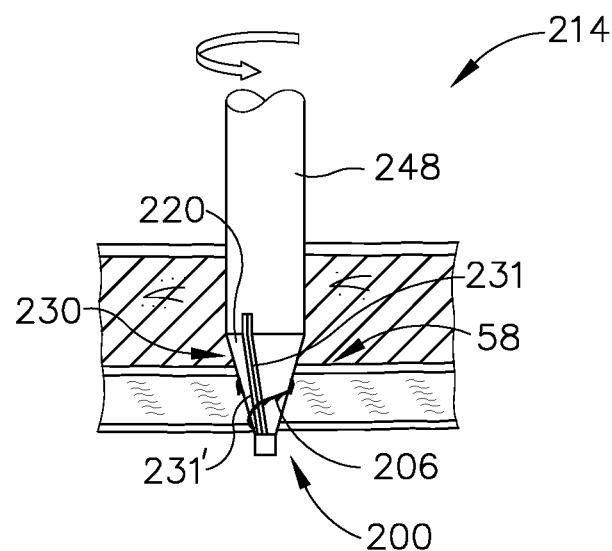
FIG. 12B depicts the partial side elevational view of the trocar assembly similar to FIG. 12A, but with the obturator and the tissue fastener rotatably driven against tissue for suturing the opening closed.
Figure 12C:
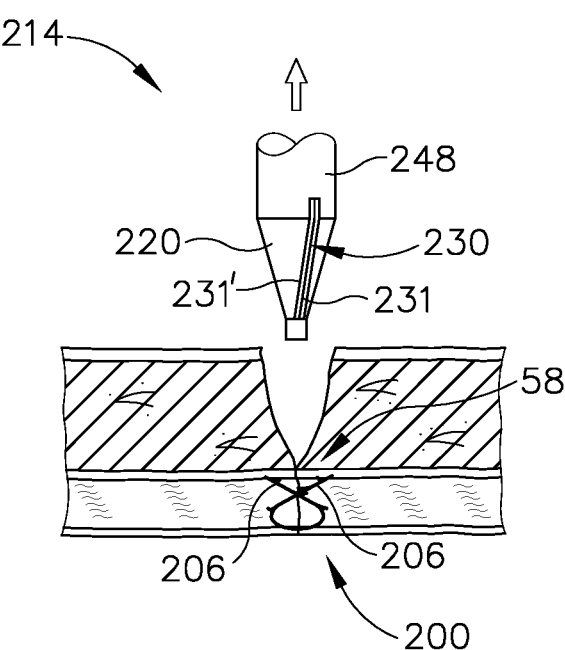
FIG. 12C depicts the partial side elevational view of the trocar assembly similar to FIG. 12B, but with the obturator retracted from the tissue opening and the tissue fastener securely fastened to the tissue to close the opening.

FIGS. 12A-12C show another exemplary alternative trocar obturator (214) including a cylindrical shaft (248), a distal tip (220) and a tissue fastener (200). Distal tip (220) is positioned along a distal end of cylindrical shaft (248), and tissue fastener (200) is releasably attached to trocar obturator (214) at distal tip (220). Cylindrical shaft (248) is configured to translate distally within trocar cannula (12) (see FIG. 1) to allow distal tip (220) to extend beyond cannula distal end opening (36) and thereby substantially uncover tissue fastener (200) from trocar cannula (12). In some other versions, trocar cannula (12) is removed from the patient and then trocar obturator (214) is subsequently inserted through the opening left by trocar cannula (12). Obturator (114) may also be used in a similar fashion, such that it is not necessarily required in all versions for obturator (114) to be disposed in trocar cannula (12) when obturator (114) deploys fastener (100) in tissue.

Trocar obturator (214) is configured to releasably secure tissue fastener (200) to distal tip (220) through the engagement of tissue fastener (200) to a second securement mechanism (230), which includes a securement shoulder (231') along a securement slot (231). In particular, securement slot (231) extends longitudinally and radially outwardly along a substantial longitudinal length of distal tip (220) and is configured to hold tissue fastener (200) on distal tip (220) until the rotatory application of a predetermined release force.

Tissue fastener (200) comprises a pair of arms (206) extending along respective helical paths from a base (202) such that arms (206) lie in varying dimensional planes from each other. Arms (206) and base (202) are generally similar to arms (106) (see FIG. 11A) and base (102) (see FIG. 11A) for engaging tissue with barbs (108) (see FIG. 11A). However, base (202) does not have slot (103) (see FIG. 11A) and each arm (206) further includes a catch member (207) extending radially inwardly toward securement slot (231). Each catch member (207) is configured to fit within securement slot (231) and releasably engage with distal tip (220) for releasably attaching tissue fastener (200) to distal tip (220). Arms (206) are configured to draw radially outwardly as the applied force increases toward the predetermined release force and thus similarly withdraw catch members (207) radially outwardly from securement slot (231). Once the applied force increases to the predetermined release force, catch members (207) fully withdraw from securement slot (231) to release tissue fastener (200) from distal tip (220). In the present example, each catch member (207) is at least one barb (108) (see FIG. 10A). However, the invention is not intended to be unnecessarily limited to the barb (108) (see FIG. 10A) being catch member (207).

In the present example, the clinician inserts trocar obturator (214) within trocar cannula (12) (see FIG. 1) and translates cylindrical shaft (248) distally therein to advance distal tip (220) beyond cannula distal end opening (36) (see FIG. 1). With distal tip (220) positioned beyond cannula end opening (36) (see FIG. 1), tissue fastener (200) contacts against tissue portions of tissue opening (58) and arms (206) press against the tissue portions of tissue opening (58), as seen in FIG. 12A-12B. In the present example, the tissue engaged by arms (206) is fascia (56) tissue of a patient's abdominal wall. Upon rotation of trocar obturator (214) with applied force less than the predetermined release force, barbs (108) (see FIG. 11A) catch the tissue portions of tissue opening (58). As the force increases, arms (206) radially deflect outwardly from the coiled, helical arrangement around distal tip (220). Rotating distal tip (220) draws the tissue portions of tissue opening (58) together as arms (206) are driven into the tissue to partially close tissue opening (58) until the applied force increases to the predetermined release force. Catch members (207) then withdraw from securement slot (231) thereby releasing tissue fastener (200) from trocar obturator (214). With tissue opening (58) partially closed (e.g., the region of tissue opening (58) at the fascia (56) is closed but not the region of tissue opening (58) that is proximal to the fascia (56)), and with tissue fastener (200) completely freed from the releasable engagement with distal tip (220) via securement slot (231), the clinician retracts trocar obturator (214) proximally through trocar cannula (12) as seen in FIG. 12C.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) a shaft extending longitudinally and having a distal end portion; and (b) a tissue fastener releasably attached to the distal end portion of the shaft, wherein the shaft is operable to rotatably drive the tissue fastener about a longitudinal axis of the shaft, wherein the tissue fastener includes: (i) a base, (ii) a first arm extending longitudinally from the base, wherein the first arm is configured to be received within a first tissue portion, (iii) a second arm extending longitudinally from the base, wherein the second arm is configured to be received within a second tissue portion, wherein the first and second arms are configured to respectively draw the first tissue portion against the second tissue portion in response to rotation of the shaft about the longitudinal axis, and (iv) a plurality of barbs extending from the first and second arms, wherein the barbs are configured to anchor the first and second arms respectively within the first and second tissue portions, wherein the distal end portion of the shaft is configured to release the tissue fastener thereby securing the first tissue portion against the second tissue portion with the tissue fastener anchored therein.

Example 2

The surgical instrument of Example 1, wherein the tissue fastener is of a bioabsorbable material.

Example 3

The surgical instrument of any one or more of Examples 1 through 2, wherein the first and second arms lie in varying dimensional planes and are configured to coil around the distal end portion.

Example 4

The surgical instrument of Example 3, wherein the first and second arms extend from the base along respective helical paths.

Example 5

The surgical instrument of any one or more of Examples 1 through 4, wherein the shaft is configured to release the tissue fastener when rotated at a predetermined release force when the distal end portion abuts a first and second tissue portion.

Example 6

The surgical instrument of Example 5, wherein the first and second arms are configured to be directed radially outwardly upon the application of the predetermined release force.

Example 7

The surgical instrument of Example 6, wherein the distal end portion of the shaft has a securement shoulder configured to receive the first and second arms such that the tissue fastener is releasably clipped onto the distal end portion.

Example 8

The surgical instrument of Example 7, wherein the securement shoulder extends along a securement slot and at least one barb comprises a catch member configured to be received within the securement slot to thereby releasably clip onto the distal end portion.

Example 9

The surgical instrument of Example 8, wherein the catch member is configured to be directed radially outwardly with the first and second arms to thereby release the distal end portion upon the application of the predetermined release force.

Example 10

The surgical instrument of any one or more of Examples 1 through 9, wherein the shaft is configured to be received in a trocar.

Example 11

The surgical instrument of Example 10, wherein the shaft is configured to translate within a cannula of the trocar from a first position to a second position, wherein the tissue fastener is configured to be covered by the cannula when the shaft is in the first position, wherein the tissue fastener is configured to extend beyond the cannula when the shaft is in the second position.

Example 12

The surgical instrument of any one or more of Examples 1 through 11, further comprising a securement hook configured to releasably attach the tissue fastener to the distal end portion.

Example 13

The surgical instrument of Example 12, wherein the shaft has a channel extending through the distal end portion to an opening, and wherein the securement hook is slidably disposed through the channel.

Example 14

The surgical instrument of Example 13, wherein the base is configured to receive the hook member through the opening such that the hook member releasably attaches the tissue fastener to the distal end portion of the shaft.

Example 15

The surgical instrument of Example 14, wherein hook member is configured to rotate within the channel to disengage the securement hook from the tissue fastener.

Example 16

A tissue fastener, comprising: (a) a body including a slot, wherein the slot is configured to releasably attach the body to a surgical instrument; (b) a first arm angularly extending from the body in a helical formation, wherein the first arm includes at least one barb protruding laterally from the first arm; and (c) a second arm angularly extending from the body in a helical formation opposite of the first arm, wherein the second arm includes at least one barb protruding laterally from the second arm; wherein the first and second arms are configured to be rotatably driven within tissue; and wherein the at least one barb of the first and second arms are configured to securely close a tissue opening when the first and second arms are rotatably driven within the tissue.

Example 17

The tissue fastener of Example 16, wherein the body and the first and second arms are formed of a bioabsorbable material.

Example 18

The tissue fastener of any one or more of Examples 16 through 17, wherein the surgical instrument is configured to release the slot when the first and second arms abut the tissue opening and the body is rotated at a predetermined release force.

Example 19

The tissue fastener of any one or more of Examples 16 through 17, wherein the first and second arms are configured to curl around the surgical instrument in varying dimensional planes about the body.

Example 20

A method of closing a tissue opening in a patient using a barbed fastener and an obturator, wherein the barbed fastener includes a pair of arms with a plurality of barbs extending therefrom, wherein the obturator includes a securement mechanism configured to removably attach the barbed fastener to the obturator, the method comprising: (a) inserting the obturator with the barbed fastener thereon into a tissue opening with a surrounding tissue portion; (b) positioning the pair of arms against the tissue portion within the tissue opening site to securely fasten the plurality of barbs to the tissue portion along varying dimensional planes; (c) rotating the barbed fastener against the tissue portions with the obturator to thereby close the tissue opening with the tissue portion being pulled together along multiple dimensional planes; and (d) disengaging the barbed fastener from the obturator via the securement mechanism.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No.

8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

The teachings presented herein may be further combined with various teachings of any one or more of the following: U.S. App. No. 15/637,690, entitled "Needle Guide Instrument with Traverse Suture Capture Feature," filed on Jun. 29, 2017, published as U.S. Pub. No. 2019/0000443 on Jan. 3, 2019, the disclosure of which is incorporated by reference herein; U.S. App. No. 15/637,702, entitled "Suture Grasping Instrument," filed on Jun. 29, 2017, published as U.S. Pub. No. 2019/0000440 on Jan. 3, 2019, issued as U.S. Pat. No. 10,639,029 on May 5, 2020, the disclosure of which is incorporated by reference herein; U.S. App. No. 15/637,683, filed on Jun. 29, 2017, published as U.S. Pub. No. 2019/0000505 on Jan. 3, 2019, issued as U.S. Pat. No. 10,639,068 on May 5, 2020, incorporated by reference above; U.S. App. No. 15,637,688, filed on Jan. 29, 2017, issued as U.S. Pat. No. 10,485,580 on Nov. 26, 2019, incorporated by reference above; U.S. App. No. 15/637,712, entitled "Suture Passing Instrument with Puncture Site Identification Feature," filed on Jun. 29, 2017, published as U.S. Pub. No. 2019/0000444 on Jan. 3, 2019, the disclosure of which is incorporated by reference herein; U.S. App. No. 15/637,696, entitled "Trocar Obturator with Transverse Needle Ports," filed on Jun. 29, 2017, published as U.S. Pub. No. 2019/0000506 on Jan. 3, 2019, the disclosure of which is incorporated by reference herein; U.S. App. No. 15/637,707, entitled "Surgical Port with Wound Closure Channels," filed on Jun. 29, 2017, issued as U.S. Pat. No. 10,568,619 on Feb. 25, 2020, the disclosure of which is incorporated by reference herein; U.S. App. No. 15/637,778, entitled "Method of Suturing a Trocar Patch Incision," filed on Jun. 29, 2017, published as U.S. Pub. No. 2019/0000496 on Jan. 3, 2019, the disclosure of which is incorporated by reference herein; and/or other patents and patent application publications incorporated by reference above.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
    (a) a shaft extending longitudinally and having a distal end portion; and
    (b) a tissue fastener releasably attached to the distal end portion of the shaft, wherein the shaft is operable to rotatably drive the tissue fastener about a longitudinal axis of the shaft, wherein the tissue fastener includes:
        (i) a base releasably attached to the distal end portion of the shaft,
        (ii) a first arm extending laterally and longitudinally from the base, wherein the first arm extends longitudinally from the base in a first direction, wherein the first arm is configured to be received within a first tissue portion,
        (iii) a second arm extending laterally and longitudinally from the base, wherein the second arm extends longitudinally from the base in the first direction, wherein the second arm is configured to be received within a second tissue portion, wherein the first and second arms are configured to respectively draw the first tissue portion against the second tissue portion in response to rotation of the shaft about the longitudinal axis, and (iv) a plurality of barbs extending from the first and second arms, wherein the barbs are configured to anchor the first and second arms respectively within the first and second tissue portions, wherein the first direction along the longitudinal axis is a proximal direction; wherein the distal end portion of the shaft is configured to release the tissue fastener thereby securing the first tissue portion against the second tissue portion with the tissue fastener anchored therein.

2. The surgical instrument of claim 1, wherein the tissue fastener is of a bioabsorbable material.

3. The surgical instrument of claim 1, wherein the first and second arms lie in varying dimensional planes and are configured to coil around the distal end portion.

4. The surgical instrument of claim 3, wherein the first and second arms extend from the base along respective helical paths.

5. The surgical instrument of claim 1, wherein the shaft is configured to release the tissue fastener when rotated at a predetermined release force when the distal end portion abuts the first and second tissue portion.

6. The surgical instrument of claim 5, wherein the first and second arms are configured to be directed radially outwardly upon the application of the predetermined release force.

7. The surgical instrument of claim 6, wherein the distal end portion of the shaft has a securement shoulder configured to receive the first and second arms such that the tissue fastener is releasably clipped onto the distal end portion.

8. The surgical instrument of claim 7, wherein the securement shoulder extends along a securement slot and at least one barb of the plurality of barbs comprises a catch member configured to be received within the securement slot to thereby releasably clip onto the distal end portion.

9. The surgical instrument of claim 8, wherein the catch member is configured to be directed radially outwardly with the first and second arms to thereby release the distal end portion upon the application of the predetermined release force.

10. The surgical instrument of claim 1, wherein the shaft is configured to be received in a trocar.

11. The surgical instrument of claim 10, wherein the shaft is configured to translate within a cannula of the trocar from a first position to a second position, wherein the tissue fastener is configured to be covered by the cannula when the shaft is in the first position, wherein the tissue fastener is configured to extend beyond the cannula when the shaft is in the second position.

12. The surgical instrument of claim 1, further comprising a securement hook configured to releasably attach the tissue fastener to the distal end portion.

13. The surgical instrument of claim 12, wherein the shaft has a channel extending through the distal end portion to an opening, and wherein the securement hook is slidably disposed through the channel.

14. The surgical instrument of claim 13, wherein the base is configured to receive the securement hook through the opening such that the securement hook releasably attaches the tissue fastener to the distal end portion of the shaft.

15. The surgical instrument of claim 14, wherein the securement hook is configured to rotate within the channel to disengage the securement hook from the tissue fastener.

16. A surgical instrument, comprising:
(a) a shaft extending along a longitudinal axis and having a distal end portion; and
(b) a tissue fastener, wherein the shaft is operable to rotatably drive the tissue fastener about the longitudinal axis of the shaft, wherein the tissue fastener includes:
(i) a base releasably attached to the distal end portion of the shaft,
(ii) a first arm extending helically from the base in a first longitudinal direction about the longitudinal axis, wherein the first arm is configured to be received within a first tissue portion,
(iii) a second arm extending helically from the base in the first longitudinal direction about the longitudinal axis, wherein the second arm is configured to be received within a second tissue portion, wherein the first and second arms are configured to respectively draw the first tissue portion against the second tissue portion in response to rotation of the shaft about the longitudinal axis, and
(iv) a plurality of barbs extending from the first and second arms, wherein the barbs are configured to anchor the first and second arms respectively within the first and second tissue portions, wherein the first direction along the longitudinal axis is a proximal direction; wherein the distal end portion of the shaft is configured to release the tissue fastener thereby securing the first tissue portion against the second tissue portion with the tissue fastener anchored therein.

17. The surgical instrument of claim 16, wherein the first arm and the second arm extend laterally in opposite directions.

18. The surgical instrument of claim 16, wherein the plurality of bards extend outwardly from their respective first and second arms.

19. A surgical instrument, comprising:
(a) a shaft extending longitudinally and having a distal end portion; and
(b) a tissue fastener, wherein the shaft is operable to rotatably drive the tissue fastener about a longitudinal axis of the shaft, wherein the tissue fastener includes:
(i) a base releasable attached to the distal end portion of the shaft,
(ii) a first arm extending laterally and longitudinally from the base, wherein the first arm terminates into a first tip, wherein the first tip is longitudinally displaced from the base in a first direction, wherein the first arm is configured to be received within a first tissue portion,
(iii) a second arm extending laterally and longitudinally from the base, wherein the second arm terminates into a second tip, wherein the second tip is longitudinally displaced from the base in the first direction, wherein the second arm is configured to be received within a second tissue portion, wherein the first and second arms are configured to respectively draw the first tissue portion against the second tissue portion in response to rotation of the shaft about the longitudinal axis, and
(iv) a plurality of barbs extending from the first and second arms, wherein the barbs are configured to anchor the first and second arms respectively within the first and second tissue portions, wherein the first direction along the longitudinal axis is a proximal direction; wherein the distal end portion of the shaft is configured to release the tissue fastener thereby securing the first tissue portion against the second tissue portion with the tissue fastener anchored therein.

\* \* \* \* \*